United States Patent [19]

Ayers et al.

[11] Patent Number: 5,397,961
[45] Date of Patent: Mar. 14, 1995

[54] APPARATUS FOR GENERATING A PULSED PLASMA IN A LIQUID MEDIUM

[76] Inventors: Richard A. Ayers, 10801 DeWitt Ct., El Cajon, Calif. 92020; Richard H. Wesley, 19511 Ricelake La., Houston, Tex. 77084

[21] Appl. No.: 169,006
[22] Filed: Dec. 20, 1993
[51] Int. Cl.⁶ .............................. H01J 7/24
[52] U.S. Cl. .................... 315/111.21; 315/111.31; 315/111.71; 210/243
[58] Field of Search .............. 210/243, 748; 422/186.21; 315/111.21, 111.31, 111.71

[56] References Cited

U.S. PATENT DOCUMENTS

| | | |
|---|---|---|
| 3,093,770 | 6/1963 | Wesley et al. |
| 3,220,873 | 11/1965 | Wesley. |
| 4,458,153 | 7/1984 | Wesley ................................ 250/435 |
| 5,026,484 | 6/1991 | Juvan ............................. 210/748 X |
| 5,302,881 | 4/1994 | O'Loughlin .................... 315/111.21 |

Primary Examiner—Robert J. Pascal
Assistant Examiner—Haissa Philogene
Attorney, Agent, or Firm—Joseph H. Roediger

[57] ABSTRACT

Apparatus for generating a pulsed plasma in a liquid medium wherein a pulse forming network is provided to supply a high energy pulse to spaced electrodes for creating a spark channel and initiating the plasma. The pulse forming network is impedance matched to the average impedance of the plasma channel established between the electrodes. The network generates a 5 to 20 microsecond pulse in the gigawatt power range to effect energy transfer to the plasma before significant expansion can occur.

19 Claims, 2 Drawing Sheets

APPARATUS FOR GENERATING A PULSED PLASMA IN A LIQUID MEDIUM

BACKGROUND OF THE INVENTION

This invention relates to apparatus for generating an extremely high pressure shock wave in a liquid medium by means of a pulsed plasma established therein.

The presence of an electrical discharge between electrodes immersed in a liquid-like medium is known to produce a "spark channel" between the electrodes. The spark channel ionizes the adjacent liquid to create a plasma therein. Among other effects, the plasma results in the production of ultrahydraulic pressure and ultraviolet radiation effects in the surrounding liquid medium. These effects have been used in a variety of ways to treat liquid-like substances in a confined environment in order to purify the liquid. One process described in U.S. Pat. No. 4,458,153 utilizes the effects of a spark discharge produced between electrodes in combination with a localized magnetic field to alter the characteristics of confined liquid substances.

On a laboratory scale, limited volumes of liquid-like substances have been treated in relatively small, confinement chambers, for example less than one liter, wherein a spark discharge is established for a brief period. While the use of small confinement chambers in combination with relatively low power sparks is useful for some small batch processing utilizing the generated radiation and the pressure effects, the extension of the length of the spark channel and impedance matching of the electrical driver network to that of the spark channel to create a larger plasma volume and energy density is a desirable goal. The application of increased power to the spaced electrodes in the chamber creates an opportunity to increase the length of the spark channel while maintaining a high energy density in the plasma. In addition, chamber design has been found to enhance the generated effects. These conditions enable the beneficial effects of the process to be applied to the treatment of larger volumes of material supplied to the confinement chamber on a continuing basis. One such apparatus for utilizing the effects of a spark channel and the created plasma to purify liquid in a continuing manner is described in my co-pending U.S. application Ser. No. 08/011,224 entitled Apparatus For Treating A Confined Liquid By Means Of A Pulse Electrical Discharge. This novel apparatus utilizes a confining vessel of unique design to increase the beneficial results obtained from a spark discharge and the resultant plasma. The invention disclosed therein permits the use of relatively large chambers having a liquid or slurry passing therethrough on a continuing basis.

Apparatus previously used to gain the benefit of the electrical characteristics of the spark channel and resultant plasma have employed a completely bounded confinement vessel for the medium. This requires fluid transfer to and from the treatment chamber in synchronism with the application of power to the electrodes in the confinement chamber thereby limiting the industrial application of the process and the potential uses of the structure. In this type of operation, the pulsed plasma created between electrodes in the confinement vessel generates an extremely high pressure shock wave in the confined liquid. However due to the fact that the vessel is bounded on all sides, the beneficial effects are experienced only by the limited volume of material contained within the vessel at the time of the creation of the plasma. In order to more fully utilize the beneficial effects created by a spark channel and resultant shock waves more distant from the spark source, it is necessary to transfer increased amounts of energy in a pulsed form to the apparatus. In addition, it is important to facilitate the transfer of this energy to the plasma to provide high energy effects in the liquid medium. Furthermore, in order for the shock wave created by the formation of the plasma to have a beneficial impact at a distance from the electrodes, a different approach is needed for the geometrical design of the shock wave launching means so as to permit high energy discharges on a repetitive basis. Repetitive high energy pulses carry the benefits resulting from the establishment of shock waves beyond the immediate vicinity of the electrodes.

Accordingly, the present invention is directed to the provision of apparatus for generating an extremely high pressure shock wave by the use of a pulsed plasma in a liquid medium without requiring a bounded vessel for the liquid. The present invention produces the high pressure shock wave in a liquid environment in a manner which enables the beneficial effects thereof to be utilized at a distance from the electrodes. In particular, the effects produced by the pulsed plasma established by the present apparatus can be utilized for the removal of biofouling and scaling from a wide variety of pipes and other structures either containing or exposed to liquids, as well as preventing or inhibiting regrowth or rescaling in these pipes or structures. In addition, the ability to create a shock wave of sufficient magnitude to enable the effects produced by the shock wave to be felt and experienced by objects outside the spark vessel enable the present apparatus to be used to fracture nearby solid substances, such as packed ice and floating ice. The shock wave produced by the present apparatus can also be used to prevent intrusion in water bodies by a wide variety of life forms which would otherwise contaminate ducts, harbors and subpens.

Therefore, it is a primary objective of this invention to provide apparatus for generating, focusing and concentrating shock waves in liquid-like substances which are not confined within the vessel in which the plasma is created. Another objective is to create a plasma between electrodes which is substantially higher in energy density and peak power over those obtained by apparatus heretofore utilized. Furthermore, the present invention enables the applied power pulse to be efficiently utilized in the creation of the plasma. The energy transfer between a pulse forming network and the plasma is enhanced. As a result of enhancement of the peak plasma pumping power employed in the shock wave launching means of the present apparatus, the beneficial effects of the shock wave can be utilized at a distance outside the shock wave launching apparatus.

Also, the present apparatus is configured to permit repetitive generation of high pressure shock waves without unduly shortening the life of the electrodes. The region in which the shock waves are launched is contoured to provide reflection and concentration of the shock waves as they are travelling from the electrodes. This feature enables the effects from the present apparatus to be utilized on large volume structures and on masses located at distances of hundreds of feet from the shock wave launching source. While the present invention is constructed to utilize high energy plasmas, it is to be noted that low level shock waves can be launched thereby at regular intervals as well.

SUMMARY OF THE INVENTION

The present invention concerns apparatus for effectively generating a high pressure shock wave in a liquid medium to produce beneficial results ill the medium at a distance from the apparatus. The apparatus contains first and second spaced electrodes for contact with a liquid medium. Means are provided for maintaining the spacing and orientation of the first and second electrodes when the electrodes are in contact with the medium and power is applied thereto.

A pulse forming electrical network is coupled between an external power supply and the first and second electrodes with output switch means for control coupled therebetween. The network has a characteristic electrical impedance which is a function of the spacing between the first and second electrodes so that the network impedance is closely matched to the characteristic impedance of the plasma when it is initially established in the medium. Following establishment, the plasma expands in size in a relatively short period of time. As a result, the impedance of the plasma which is primarily resistive decreases and the energy density thereof decreases accordingly. In order to produce a plasma with a high energy density, the power transfer has to occur several microseconds (10–20) after the initiation of the plasma before it expands significantly in volume. The ability of the apparatus to create a high pressure shock wave in the medium is determined by the effectiveness of the energy transfer in the initial stages of the generation of the plasma.

The actuation of the output switch means provides a pulse of energy to the electrodes from storage capacitor means through the series inductances of the pulse forming network, the output switch means and the power bus coupling the pulse forming network and switch means to the first and second electrodes. The switching means can be repetitively cycled to launch a series of shock waves into the liquid.

The shock wave is launched as a result of the creation of the plasma and its rapid expansion. The wave travels from the region containing the plasma into the surrounding liquid medium. The apparatus containing the electrodes is provided with a reflector section proximate thereto which directs the shock wave through an adjacent concentrating section to an output port. The output port either communicates directly with the adjacent liquid-like material or, in some cases, can be provided with a diaphragm to transfer the shock wave to an adjacent physical structure such as a pipeline.

The present apparatus enables the energy to be transferred to the plasma at the point in time when the shock wave is being created. The matching of the impedance of the pulse forming network with the impedance of the plasma channel at the time of creation is primarily a function of the electrode spacing. The effects of the high pressure shock wave launched within the apparatus are experienced by an adjacent volume of liquid medium. The extremely high electrohydraulic pressure created by the shock wave can be utilized to control marine life, provide purification of the adjacent liquid medium as well as providing sufficient force to fracture solid phase materials nearby.

Further features and advantages of the present invention will become more readily apparent from the following detailed description of the preferred embodiments thereof when taken in conjunction with the accompanying drawings.

DESCRIPTION OF THE PREFERRED EMBODIMENTS

Figure 1:
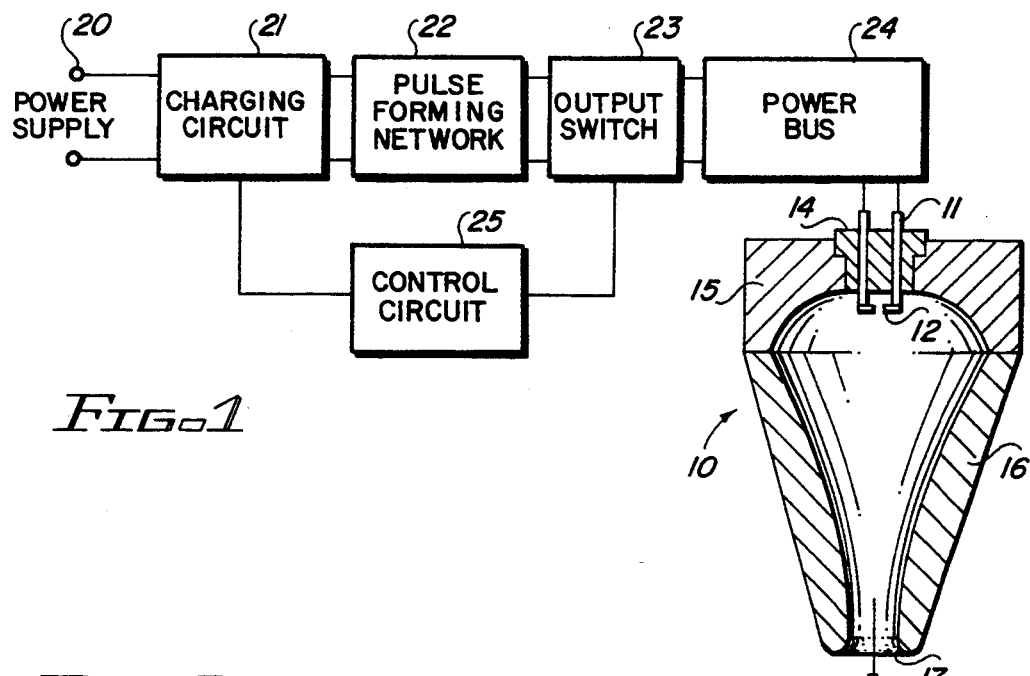
FIG. 1 is a cross sectional view showing one embodiment of the invention and the block schematic thereof.

Referring now to FIG. 1, the novel apparatus for generating a high pressure shock wave in a liquid medium is shown comprising a shock wave generator (SWG) 10 which includes a spark head 15 having a centrally located insulating block 14 located therein. The first and second electrodes 11 are mounted in the insulating block 14 and are in a generally parallel relationship, co-axial spacing being another preferred configuration. Each electrode has a tip 12 which may be removably affixed thereto and oriented so as to be orthogonal to the corresponding electrode.

The spark head 15 has an inner curved surface from which the electrodes protrude. The region bounded by the concave inner surface of the spark head contains a liquid medium during normal operation of the apparatus. The SWG 10 also includes a concentrator 16 shown having proximal and distal ends with the proximal end affixed to the spark head 15. The inner surface of the concentrator is shown to be inwardly inclined toward its distal end. An opening 17 is provided in the distal end of the concentrator shown in FIG. 1. The concentrator has an inwardly tapered inner surface which is described as a curved surface of revolution about the central axis of the concentrator.

As mentioned, the SWG 10 for the liquid medium is shown as two distinct parts; the spark head 15 and the concentrator 16. Each part is fabricated from a high tensile, nonfatiguing metal alloy. The two part configuration is favored from the standpoint of simplifying the manufacturing process therefor. However, it is to be noted that a single unitary SWG can be utilized if desired. For reasons that will later become apparent, it is important to have the electrodes 11 in substantial parallel alignment with the central axis of the concentrator section. In operation, multiple effects including the generation of significant pressures within the medium contained in the confinement chamber will tend to distort the configuration of nonaxially aligned electrodes. Removable tips 12 which may be secured by threaded fasteners (not shown) to the respective electrode are preferred to enable any degradation of the tip occurring from the establishment of a spark channel therebetween to be readily corrected by the removal and replacement of the electrode tips without requiring replacement of the electrode. A coaxial electrode may also be utilized wherein a central electrode is employed with a concentric outer conductor.

The power to operate the subject invention is obtained from power supply 20 which is coupled to a charging circuit 21. The charging circuit is activated by the control circuit 25 to provide a charging current to pulse forming network 22. The charging circuit may utilize a step-up transformer with a high voltage, three phrase bridge rectifier to supply the charging current to the pulse forming network or may be of a more advanced design such as a conventional solid state, high frequency inverter which can maintain unity power factor during the charge cycle. A number of suitable charging means are known and further discussion thereof is not believed necessary.

Figure 2:
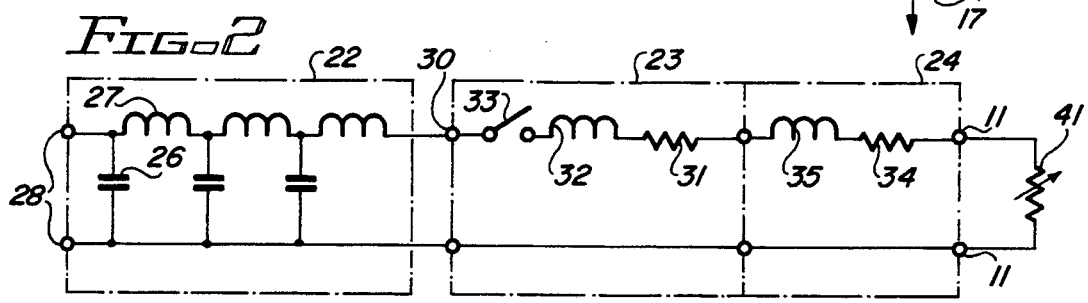
FIG. 2 is an electrical schematic of the pulse forming network used in the embodiment of FIG. 1.

The pulse forming network 22 which includes both inductive elements and capacitive elements is shown in further detail in FIG. 2. The network 22 includes a pair of input terminals 28 which are coupled to the charging circuit 21 of FIG. 1 and contain a number of capacitors 26 coupled therebetween in a ladder network. Series inductors 27 are provided between adjacent capacitors 26. The pulse forming network is charged to a preset voltage level by the charging means 21 and stores energy in the network of capacitors 26. The pulse forming network is connected by terminals 30 to the output switch 23. Output switch 23 includes the distributed impedances shown as resistor 31, inductor 32 and the switch 33 in series. The power bus 24 which transfers the power pulse to the SWG chamber is shown coupled to the variable resistor 41 which represents the resistance of the medium between the electrodes 11. The power bus also includes a distributed inductance 35 and resistance 34. The significance of these impedances, both distributed and lumped, will become more apparent from the description of the operation of the invention.

Figure 3:
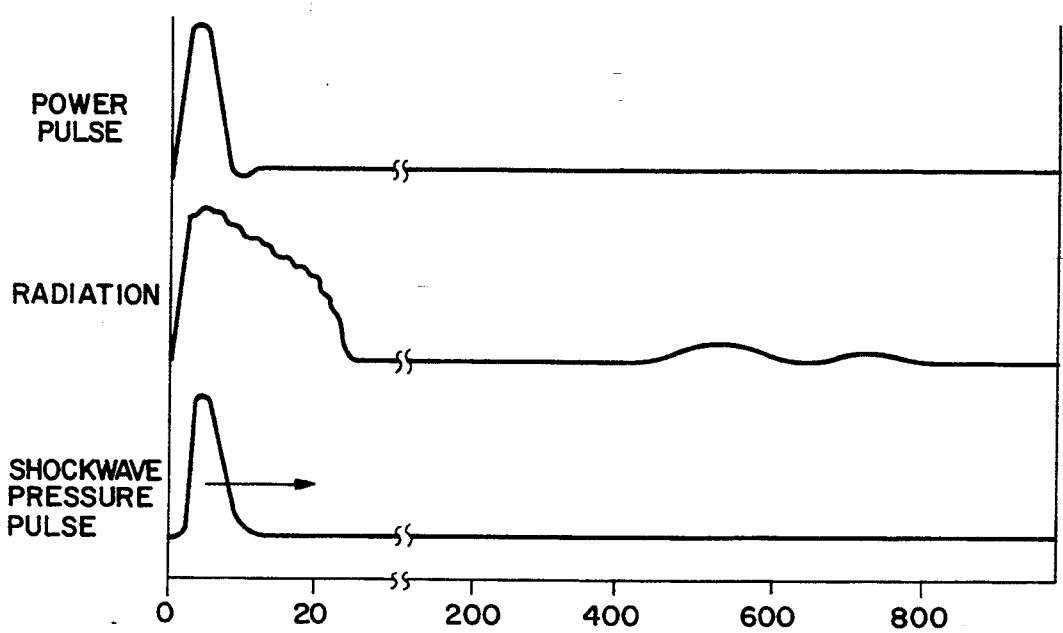
FIG. 3 is a series of wave forms showing the effects of the plasma generated within the shock wave launching vessel of the embodiment of FIG. 1.

The actuation of output switch 23 causes the stored energy in the capacitors of the pulse forming network to appear across the variable resistor 41 as a power pulse shown in FIG. 3. This power pulse causes a spark channel to form in the liquid medium between the electrode tips. To enhance the transfer of power, the output switch 23 and the power bus 24 are selected to very little resistive and inductive components to the total circuit impedance presented to the electrodes. Also, the control circuit 25 is utilized to synchronize and regulate the charging of the pulse forming network and the transfer of power to the electrodes in the SWG. The control circuit may include a clock circuit in order to establish regular intervals between pulses as well as data sample rates if the circuit should include a microprocessor. The monitoring of operating parameters and comparing sample data with set point boundaries can be utilized as desired based on the particular application for which the invention is being utilized. For the purposes of this disclosure, it is only necessary to point out that the charging circuit 21 and output switch 23 operate alternatively so that the pulse forming network 22 can receive and store sufficient energy between discharge intervals to supply a power pulse to the electrodes.

The electrical equivalent circuit shown in FIG. 2 is utilized to provide the energy transfer frown the external power supply 20 to the pair of electrodes 11 in the chamber. Since the electric potential provided to the electrodes initiates a spark channel between electrodes and causes the ionization of the liquid medium to form a plasma, the pulse forming network is required to provide a substantial power pulse. In prior apparatus used in connection with the establishment of a plasma in a liquid medium, the transfer of energy was not efficiently and effectively accomplished thereby limiting useful application thereof. In the present invention, the SWG 10 is designed to propagate the varied effects generated by the plasma to regions outside. To obtain this result, the impedance of the pulse forming network 22 is matched to the average resistance presented to the equivalent circuit of FIG. 2 by the plasma channel during the relatively short duration of the power pulse. Not only is the impedance of the pulse forming network taken into consideration in matching impedances, but also that of the switching means with its inductive and resistive components and the resistive and inductive components of the power bus. In the embodiment shown, the inductive and resistive components of the switching means 23 and power bus 24 comprise about five percent of the total impedance. The contribution of the power bus is determined by the physical constraints of the particular application and are related to the distance between the electrical circuitry and the electrodes.

During the early formation of the plasma between electrodes, typically the first microsecond, the resistance shown as variable resistance 41 in FIG. 2 drops from a few ohms to the 100 milliohm range. The pulse forming network does see a brief initial time of high resistance loading which drops by an order of magnitude. The energy requirement of the apparatus is typically between 10–100 kilojoules occurring in a pulse width of approximately 10 to 20 microseconds. The equation for the pulse width for the power pulse of this energy level provided by the pulse forming network is $T = 2(L_T \times C_T)^{0.5}$. In the pulse forming network shown in FIG. 2 utilizing three capacitive elements 26, the total value of capacitance is calculated to be about 135 microfarads so that each individual capacitor is 45 microfarads. The total circuit inductance for the 10 microsecond embodiment is approximately 150 nanohenries so that each inductive element 27 would be somewhat less than 50 nanohenries for the embodiment shown. The total inductance takes into account the distributed inductance shown as inductors 32 and 35 in FIG. 2. These components provide a pulse forming network having an impedance of approximately 34 milliohms. When operating this network in the 20,000 volt range, the energy stored in the capacitive elements is over 25 kilojoules, a level sufficient for most uses of the invention.

At the moment that the output switch 23 is actuated by the control circuit 25, the energy stored in the pulse forming network is provided to the electrodes 11 in the SWG. A spark discharge occurs between the electrode tips which develops a high pressure plasma channel. The pulse creating the plasma has a peak power level in excess of a gigawatt and maintains this level for intervals of 5–20 microseconds. The energy transfer is required to take place during this initial period because the plasma channel expands and increases in volume so that high energy densities are difficult or unlikely to be achieved during longer initial periods.

The present invention utilizes a pulse forming network having a characteristic impedance which is a function of the length of the plasma during the power transfer period. Plasma length is determined by the spacing between the first and second electrodes 11 in the SWG. The resistance of the established plasma channel is determined for a particular medium as a ratio of length of the plasma channel to the area thereof. The plasma channel grows as an approximate square root of the time during which it is observed. Thus, energy transfer to the electrodes takes place during the 10–20 microsecond time domain to achieve high energy density. The time constant for the pulse forming network is determined by the square root of the product of all of the inductors and all of the capacitors. The characteristic impedance of the network is the square root of the ratio of the inductance to the capacitance and is made to approximate the resistance of the plasma between electrodes during the time constant interval.

The effective transfer of energy to the plasma during its initial formation enables the present invention to produce enhanced effects downstream in the medium both within and outside of the SWG. The first direct effect generated by the plasma is a strong burst of radiation which is somewhat longer than the actual pumping time due to the highly ionized state of the plasma. The second and most important effect produced by the present invention is that of launching a shock wave with an initial pressure peak of nearly 1 million atmospheres as it breaks away from the expanding channel during the pumping period. As this supersonic wave front propagates outwardly from the plasma channel it is reflected by the concave inner surface of the spark head and deflected by the tapered inner surface of the concentrator section as it travels through the SWG in a few hundreds of microseconds. During propagation through the SWG, an extremely high compressive component resides in the region of the leading edge. The compressive component of the shock wave exits the concentrator at the opening at the bottom of the embodiment in FIG. 1 and is transmitted into the adjacent liquid medium and propagates outwardly therefrom.

The compressive component of the shock wave is useful in fracturing solids suspended in the liquid medium thereby reducing particle size. In addition, the shock wave can be utilized to break down large molecules and microorganisms in liquids. The effects produced by the power pulse are shown in the wave forms of FIG. 3 with the duration of the power pulse of about 10 microseconds. The shock wave pressure pulse is shown with the directional arrow to indicate that it continues to travel out of the SWG 10. The radiation effects are completed in an interval of approximately 20 microseconds.

By utilizing the present invention and providing a high peak power to the electrodes during a shortened plasma pumping time of approximately 10 to 20 microseconds, the effects of the plasma are enhanced. The energy is transferred during a pumping time that is shortened so that the energy density of the plasma is relatively high. The combination of matching the impedance of the pulse forming network to the resistance of the plasma channel during this shortened period when the energy density is high enables the apparatus to create a shock wave which produces results outside the SWG 10. The shock waves exhibit initial pressures at over 1 million atmospheres thereby enabling applications of the device to be expanded beyond those utilizing bounded chambers.

Figure 4:
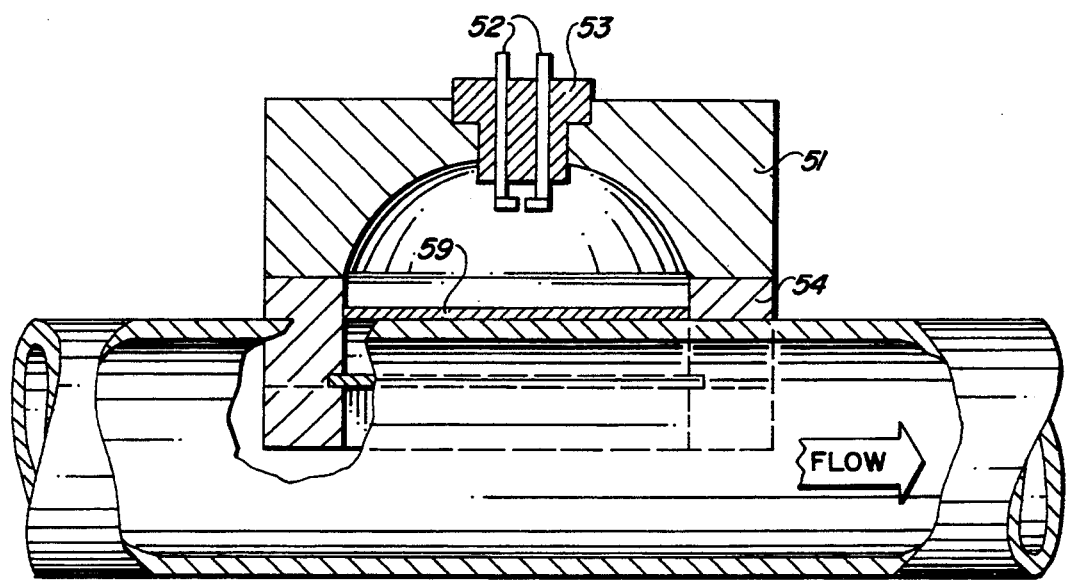
FIGS. 4 and 5 are cross sectional views of a second embodiment of the invention.
Figure 5:
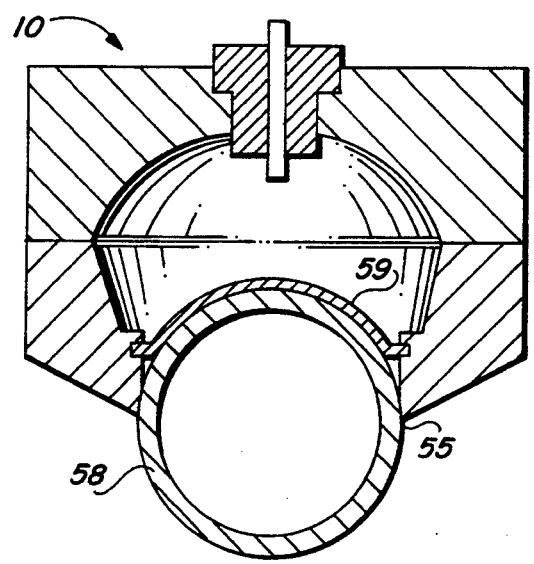

A second embodiment of the invention illustrating that the effects produced by the present invention can be utilized outside bounded chambers is shown in FIGS. 4 and 5. The SWG containing a liquid medium includes a reflector section 51 with the electrodes 52 included in an insulating block 53. The inline configuration of the electrodes is maintained to prevent the shock waves from distorting the electrodes and altering the distance between the electrode tips during operation. The concentrator section 54 is provided with a elongated opening 55 that receives a section of pipe 58. A flexible diaphragm 59 is mounted ill the side and end walls of the confinement section so that it conformably adapts to the outside surface of pipe 58. This conformance is seen more clearly from the cross sectional view of the apparatus as shown in FIG. 5. The closure of switch 23 in the circuit of FIG. 2 results in a spark channel and the establishment of a plasma between electrode tips. The shock wave is generated and impinges on the diaphragm 59 which is conformably placed on the pipe. The density of diaphragm 59 is selected to be matched to the liquid medium, usually approximately 1.0. As a result, the shock wave passes through diaphragm 59 to the pipe or other structure without reflection back into the SWG. In practice, a large mismatch of transmitting liquid to diaphragm densities is to be avoided as it would cause both a destructive force to act upon the diaphragm as well as to reduce the shock wave pressure at the pipe or structure wall.

The change in pressure at the leading edge of the shock wave is transmitted through the combination of diaphragm 59 to pipe 58. The apparatus can be used to descale the interior surfaces of the pipe, reduce the particle size of slurried materials flowing through the pipe or, in some cases, change the molecular structure of the material in the pipeline. The side walls of the concentrator section of the confinement chamber in the embodiment of FIGS. 4 and 5 have an inward taper in one direction to focus the shock wave and enhance performance of the invention. It is to be noted that the side walls extend downwardly below the diaphragm to serve as guide means for orienting the apparatus and promoting effective contact with the adjacent pipe.

While the above description has referred to specific embodiments of the invention, it is to be noted that modifications and variations may be made therein without departing from the scope of the invention as claimed.

We claim:

1. Apparatus for generating a high pressure shock wave in a liquid medium which comprises:
    (a) first and second spaced electrodes for contacting the liquid medium;
    (b) means for maintaining the spacing of the first and second electrodes when said electrodes are in contact with the medium, said means including a spark head having a curved surface from which said spaced electrodes protrude;
    (c) a pulse-forming network coupled between a power supply and the first and second electrodes for initiating a spark discharge therebetween, said network having a characteristic impedance which is a function of the spacing between the first and second electrodes; and
    (d) output switch means connected between the pulse-forming network and at least one of the electrodes, the actuation of said output switch means providing a pulse of energy to said electrodes whereby a plasma is created in that portion of the medium between the electrodes, the plasma generating a high pressure shock wave in said medium.

2. The invention in accordance with claim 1 wherein said pulse forming network includes at least one storage capacitor and at least one series inductor, the ratio of the magnitudes of said series inductor to said storage capacitor being a function of the spacing between the electrodes.

3. The invention in accordance with claim 2 wherein said pulse forming network includes a plurality of storage capacitors and a plurality of series inductors coupled between a power supply and the output switch means, the ratio of the sums of the magnitudes of said series inductors to that of said storage capacitors being a function of the spacing between the electrodes.

4. The invention in accordance with claim 3 further comprising a power bus for coupling the pulse forming network and output switch means to the electrodes, the inductances of the power bus and the output switch means being added to said sum of the magnitudes of the series inductors in the pulse forming network.

5. The invention in accordance with claim 4 further comprising control means coupled to the output switch means for establishing the tinting of repetitive pulses of energy provided to said electrodes.

6. The invention in accordance with claim 1 wherein the curved surface of said spark head is concave.

7. The invention in accordance with claim 6 further comprising a concentrator having proximal and distal ends and a central axis extending therebetween along which the shock wave travels, said proximal end being affixed to the spark head.

8. The invention in accordance with claim 7 wherein said means for maintaining the spacing of the first and second electrodes further comprises an insulating block for receiving the first and second electrodes therein, said insulating block being centrally received in the spark head.

9. The invention in accordance with claim 8 wherein said first and second electrodes protrude from the spark head so as to be parallel to the axis of the concentrator.

10. The invention in accordance with claim 9 wherein said first and second electrodes have removable tips.

11. Tile invention in accordance with claim 10 wherein said first and second electrodes have tips positioned orthogonal to the corresponding electrodes, the distance between tips defining the length of the plasma created by the spark discharge.

12. The invention in accordance with claim 7 wherein said concentrator has a curved inner surface for contact with the adjacent liquid medium, said inner surface being inwardly inclined toward the distal end.

13. The invention in accordance with claim 12 wherein the inner surface is a curved surface of revolution about the central axis of the concentrator.

14. The invention in accordance with claim 13 wherein the concentrator is provided with an opening at its distal end for the passage of the shock wave therethrough.

15. The invention in accordance with claim 14 further comprising a diaphragm mounted ill the opening at the distal end of the concentrator.

16. The invention in accordance with claim 6 further comprising a concentrator affixed to the spark head, said concentrator containing an inner bounded region having an opening therein, and a diaphragm located in said opening.

17. The invention in accordance with claim 16 wherein said means for maintaining the spacing of the first and second electrodes further comprises an insulating block for receiving the first and second electrodes therein, said insulating block being centrally received in the spark head.

18. The invention in accordance with claim 17 wherein said concentrator contains inwardly inclined wails to concentrate the shock wave produced by the plasma at said diaphragm.

19. The invention in accordance with claim 18 wherein said concentrator includes guide means extending beyond the diaphragm for promoting contact between the diaphragm and an adjacent object.

* * * * *